(12) United States Patent
Pranger et al.

(10) Patent No.: US 7,320,321 B2
(45) Date of Patent: Jan. 22, 2008

(54) SELF-CONTAINED MICROMECHANICAL VENTILATOR

(75) Inventors: L. Alex Pranger, Gaithersburg, MD (US); William P. Wiesmann, Washington, DC (US); Adrian R. Urias, Gaithersburg, MD (US)

(73) Assignee: Automedx Inc., Germantown, MD (US)

( * ) Notice: Subject to any disclaimer, the term of this patent is extended or adjusted under 35 U.S.C. 154(b) by 716 days.

(21) Appl. No.: 10/787,522

(22) Filed: Feb. 26, 2004

(65) Prior Publication Data

US 2004/0221845 A1    Nov. 11, 2004

Related U.S. Application Data

(63) Continuation-in-part of application No. 10/228,166, filed on Aug. 26, 2002, now Pat. No. 7,080,646.

(51) Int. Cl.
*A61M 16/00*    (2006.01)

(52) U.S. Cl. ............... 128/204.23; 128/204.18; 128/204.26

(58) Field of Classification Search ............... 128/200.14–200.24, 203.12, 203.23, 204.18, 128/204.21, 204.22, 204.23, 205.24, 207.14–207.18
See application file for complete search history.

(56) References Cited

U.S. PATENT DOCUMENTS

| | | | | |
|---|---|---|---|---|
| 4,080,103 A | * | 3/1978 | Bird | 417/3 |
| 4,592,349 A | * | 6/1986 | Bird | 128/204.25 |
| 4,681,099 A | * | 7/1987 | Sato et al. | 128/204.23 |
| 5,868,133 A | * | 2/1999 | DeVries et al. | 128/204.21 |
| 7,080,646 B2 | * | 7/2006 | Wiesmann et al. | 128/204.26 |
| 2003/0172931 A1 | * | 9/2003 | Kerechanin et al. | 128/204.18 |

* cited by examiner

*Primary Examiner*—Steven O. Douglas
(74) *Attorney, Agent, or Firm*—Abanti Bhattacharyya, Esq.; Bartunek & Bhattacharyya, Ltd.

(57) ABSTRACT

The portable ventilator of the present invention provide a hands-free ventilatory support device in critical care, emergency and resource limited environments. The portable ventilator utilizes ambient air and includes a two dual head compressor system to provide a consistent air supply to the patient. The ventilator device is battery operated and is capable of providing up to 60 minutes of care. In a preferred embodiment, the portable ventilator of the present invention also includes a pneumatic subsystem, a control subsystem, a power subsystem and an alarm subsystem. The portable ventilator of the preferred embodiment includes a dual head and single head compressor system that operates alternatively, to provide a consistent and continuous inhalation and exhalation cycle.

11 Claims, 12 Drawing Sheets

SELF-CONTAINED MICROMECHANICAL VENTILATOR

This application is a continuation-in-part of Ser. No. 10/228,166, filed Aug. 26, 2002, now U.S. Pat. No. 7,080,646.

BACKGROUND OF THE INVENTION

Immediate medical care can save the lives of countless accident victims and military personnel. In the emergency medical services arena, there has long been an emphasis on the golden hour during which a patient must receive definitive medical attention. However, definitive medical attention is often limited, because of the lack of necessary equipment. While state of the art medical equipment can be found in medical facilities, such is not the case in emergency situations or military applications. This is particularly true in the area of ventilators.

Inspiration-only ventilators are known and widely used in hospital settings as they provide useful breathing circuits while minimizing the amount of oxygen utilized in treating the patient.

Current ventilators are generally designed for stationary, medical facilities. They are heavy, cumbersome and ill suited for portable applications. Most ventilators utilize medical grade air or highly flammable, compressed canisters of oxygen for its oxygen sources. These tanks air/oxygen are heavy, cumbersome, and unsuitable for transport. Prior-art ventilators also require large power sources, making them even less suitable for quick, on-site use. Lastly, most known ventilators require operation by trained personnel in treatment environments, where additional equipment and resources are easily available.

For example, U.S. Pat. No. 5,664,563 to Schroeder, et al., disclose a computer controlled pneumatic ventilator system that includes a double venturi drive and a disposable breathing circuit. The double venturi drive provides quicker completion of the exhalation phase leading to an overall improved breathing circuit. The disposable breathing circuit allows the ventilator to be utilized by multiple patients without risk of contamination. This device utilizes canistered oxygen sources. This device also would be rendered inoperable under the conditions anticipated by the present invention.

Therefore, there is a need for portable ventilators that overcome the disadvantages of the existing stationary ventilators.

The following portable ventilators address some of the needs discussed above. U.S. Pat. Nos. 6,152,135, 5,881,722 and 5,868,133 to DeVries, et al., discloses a portable ventilator device that utilizes ambient air through a filter and a compressor system. The compressor operates continuously to provide air only during inspiration. The DeVries, et al., devices are utilized in hospital settings and are intended to provide a patient with mobility when using the ventilator. Since these devices are not directed to on-site emergency use, they provide closed loop control, sophisticated valve systems and circuitry that would render them inoperable under the types of emergency conditions anticipated by the present invention.

The references cited above recognize the need for portable ventilators that provide a consistent breathing circuit. As is the case with most portable ventilators, these devices provide breathing circuits including valve systems and an oxygen source. However, these devices lack the means by which they can be quickly facilitated in emergency situations where there are no stationary sources of power. Secondly, most of these devices depend on canister-style oxygen sources, which are cumbersome, and lessen the ability of the ventilators to be truly portable. Thirdly, the prior art ventilators do not provide breathing circuits that can be continuously used in the absence of stationary power sources. These and other drawbacks are overcome by the present invention as will be discussed, below.

SUMMARY OF THE INVENTION

It is therefore an objective of this invention to provide a portable ventilator that provides short-term ventilatory support.

It is another objective of the present invention to provide a portable ventilator that includes a pneumatic subsystem, a power subsystem and a sensor subsystem.

It is another objective of the present invention to provide a portable ventilator wherein the pneumatic subsystem includes two dual head compressor for increased air output.

It is another objective of the present invention to provide a portable ventilator wherein the pneumatic subsystem includes an accumulator.

It is another objective of the present invention to provide a portable ventilator that is a disposable one-use device having an indefinite shelf life.

It is also another objective of the present invention to provide a portable ventilator that includes a pneumatic subsystem, a power subsystem, a control subsystem and an alarm subsystem.

It is another objective of the present invention to provide a portable ventilator wherein the pneumatic subsystem includes one dual head compressor for increased air output and a means for relieving air manifold pressure with a single head compressor, thereby eliminating the need for an accumulator.

It is another objective of the present invention to provide a portable ventilator wherein the power subsystem includes a battery source and a jack that allows the ventilator to access an external power source, where the battery or the external power source is used to power the pneumatic, control and alarm subsystems.

It is another objective of the present invention to provide a portable ventilator wherein the power subsystem also includes a power conditioning circuit to eliminate fluctuating voltages to the control subsystem.

It is also another objective of the present invention to provide a portable ventilator wherein the control subsystem includes a timing circuit and a relay switch to control the on-off cycle of the dual-head and single head compressors.

It is also another objective of the present invention to provide a portable ventilator wherein the alarm subsystem is capable of visually indicating repairable, non-repairable and patient based problems as well as an audible alarm.

It is another objective of the present invention to provide a portable ventilator that is a disposable one-use device or a refurbished device having an indefinite shelf life.

These and other objectives have been described in the detailed description provided below.

DETAILED DESCRIPTION OF THE EMBODIMENTS

Figure 1:
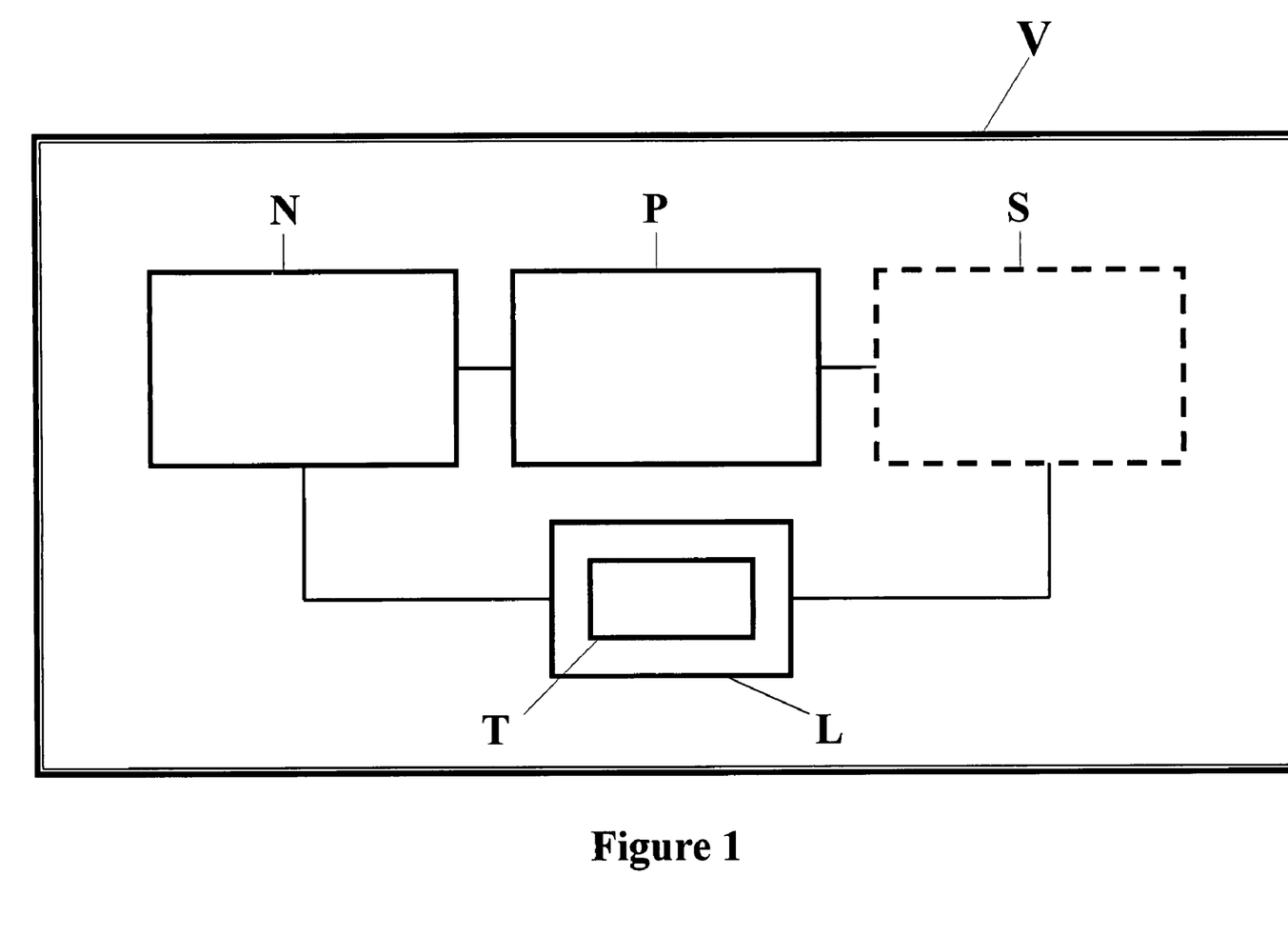
FIG. 1 is a schematic of the portable ventilator, the pneumatic subsystem, the power subsystem and the sensor subsystem.

The present invention is a portable ventilator that provides short-term ventilatory support to one or more patients for the management of trauma or respiratory paralysis. As shown in FIG. 1, the portable ventilator V assures consistent tidal volume and respiratory rate and provides hands free operational capabilities. The portable ventilator V is a fully functional multi-mode device suited for field hospital or forward surgical units, where experienced personnel can utilize the multi-mode capabilities unique to this device. Portable ventilator V is also suitable for use by untrained personnel, and in particularly useful in resource-limited environments. Additionally, the portable ventilator V can be configured as a disposable one-use device that has an indefinite shelf life.

Also in FIG. 1, the portable ventilator V of the present invention includes a pneumatic subsystem N, a power subsystem P, and a sensor subsystem S. Each of these systems shall be described below.

Figure 2:
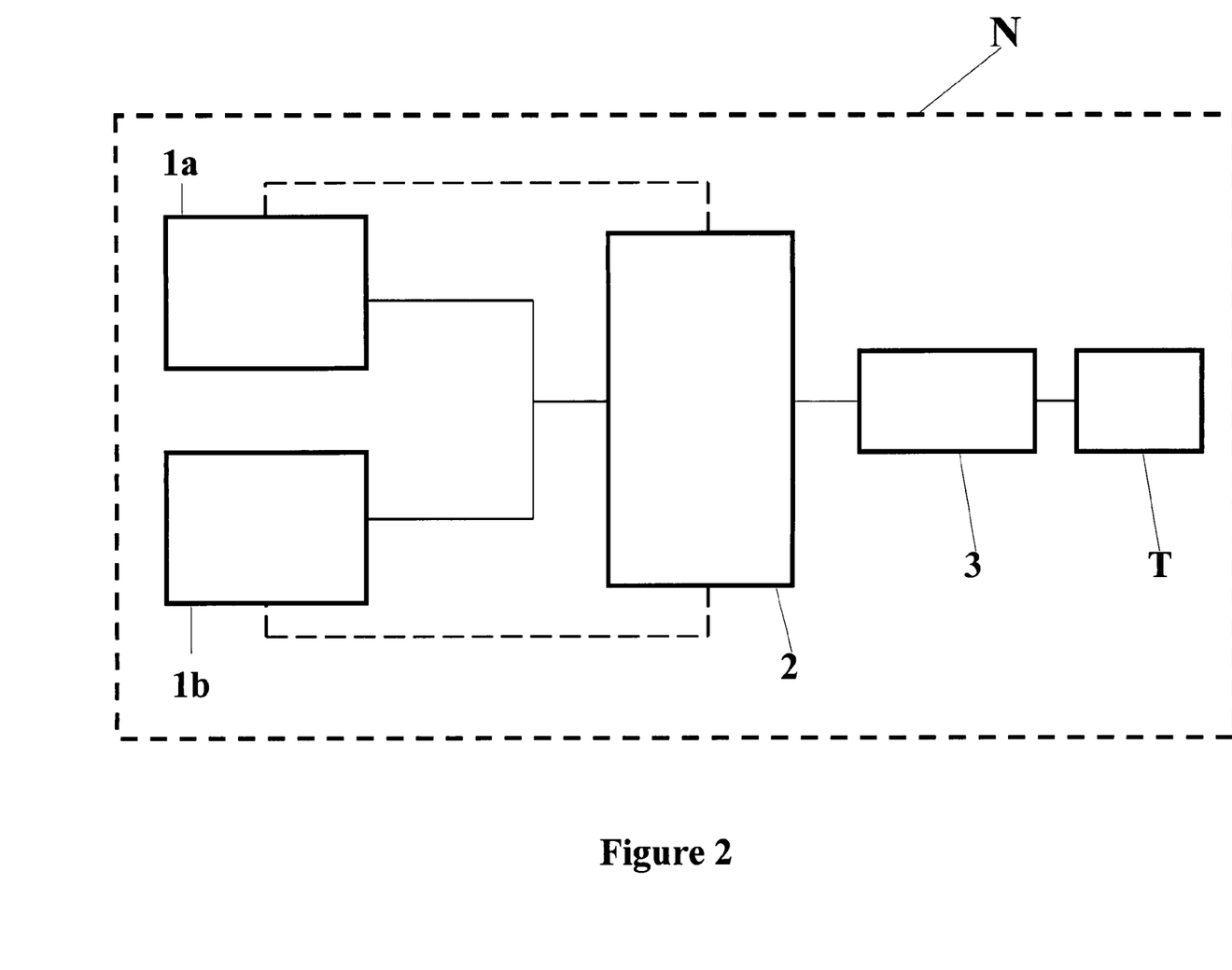
FIG. 2 is a schematic of the pneumatic subsystem shown in FIG. 1.

The Pneumatic Subsystem:

As shown in FIG. 2, the pneumatic subsystem N includes two dual head air compressors 1a and 1b for increased air output. Ambient or NVC filtered air is drawn into the dual head compressors 1a and 1b and compressed. The compressed air exits 1a and 1b and enters into the accumulator tank 2. An accumulator tank 2 is connected to each of the compressors 1a and 1b to act as a pneumatic holding area for the combined outputs (4 in total) of compressors 1a and 1b. The accumulator tank 2 overcomes the inconsistent nature of the phasing of the pressure waves inherent with dual head air compressors and prevents compressors 1a and 1b outputs from canceling each other. The accumulator tank 2 is further connected to a connector system 3. Since the compressors 1a and 1b function as constant-flow rates over a wide range of physiologic pressures, the connector system 3 provides constant, total airflow through the accumulator 2 to the user, for a necessary period of time. The periods of time are controlled through a timing circuit T that is part of a logic board B.

The Logic Board:

The logic board B includes timing circuit T and is connected to the power subsystem P. Logic board B controls power to compressors 1a and 1b in order to turn 1a and 1b on and off. Duration of the on-time of compressors 1a and 1b determines the amount of air that is delivered to the user. The logic board B utilizes analog logic and does not require microprocessor control. The logic board B is also connected to the sensor subsystem S.

Figure 3:
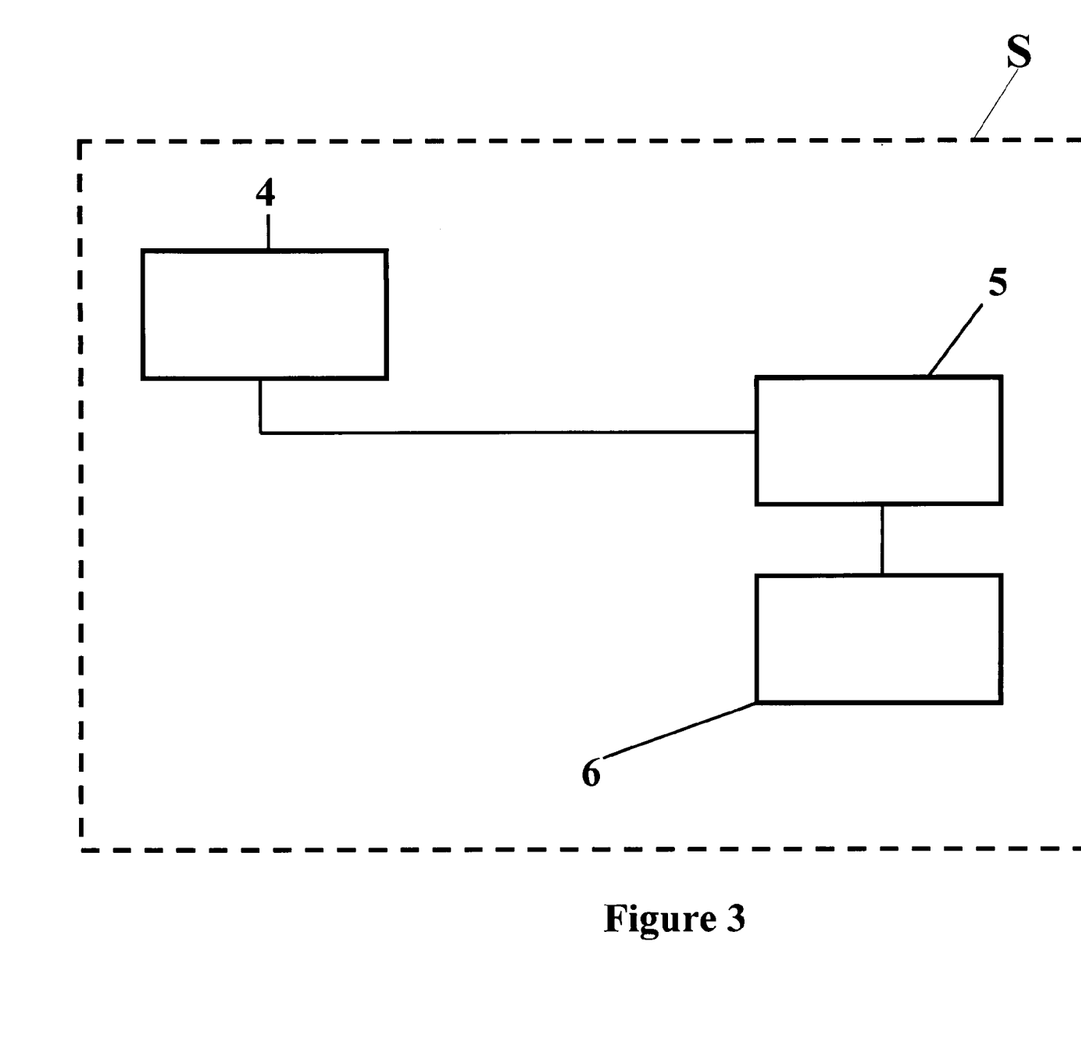
FIG. 3 is a schematic of the power subsystem shown in FIG. 1.

The Sensor Subsystem:

As shown in FIG. 3, the portable ventilator V includes a sensor subsystem S that provides critical care monitoring and support critically ill patients in the emergency situations. The sensor subsystem S includes an airflow sensor 4 that detects loss of connection of the portable ventilator V from the patient's face mask or endotracheal tube. The sensor subsystem S also includes an airway pressure sensor 5. The pressure sensor 5 provides the desirable function of detecting the end of a previous breath (inhaled) in the user, so that air delivery can be delayed until the completion of the previous breath. An airflow sensor 6 is used to detect the cessation of exhalation of the previous breath if the scheduled start time for the next breath is not completed. The sensor subsystem S may be located within the ventilator V or be exterior to ventilator V.

Figure 4:
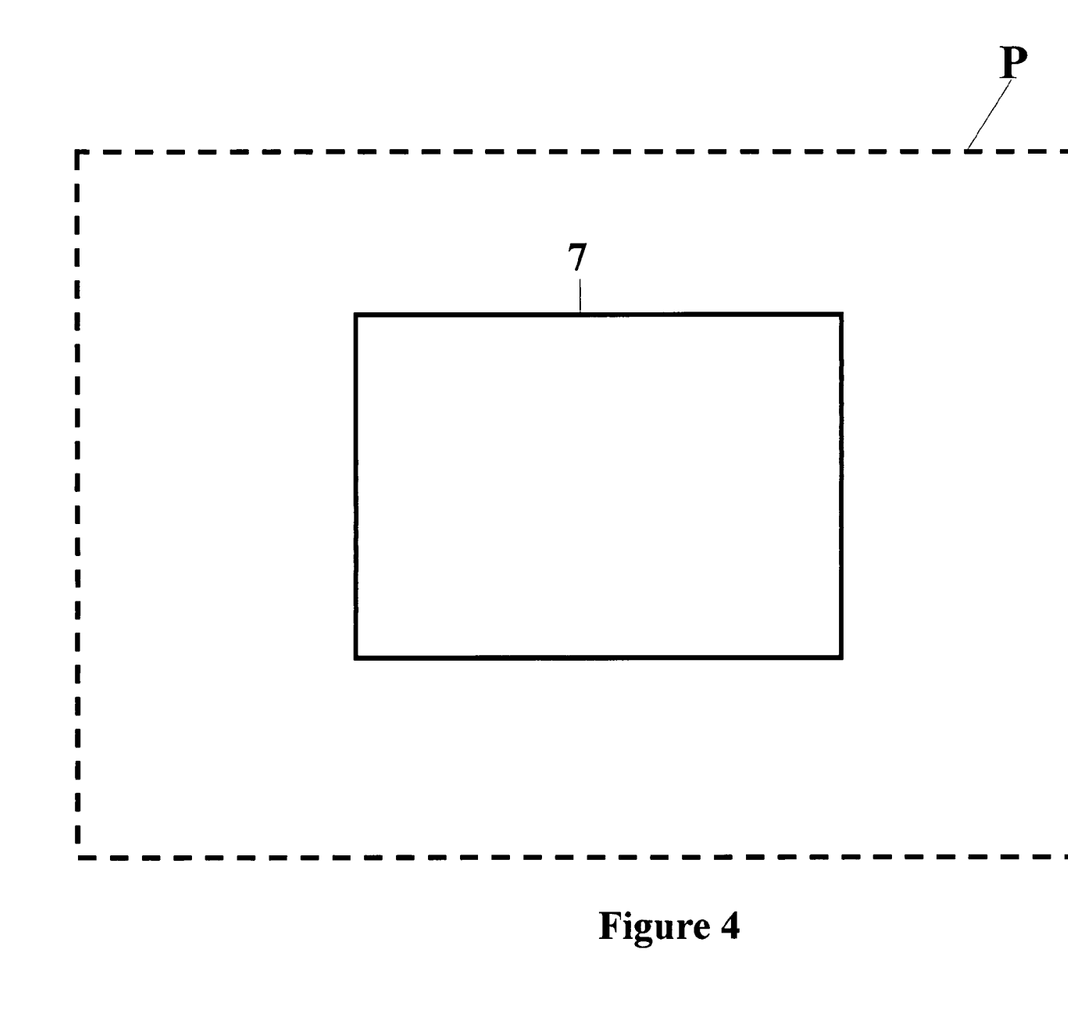
FIG. 4 is a schematic of the sensor subsystem shown in FIG. 1.

The Power Subsystem:

As shown in FIG. 4, the power subsystem P of the portable ventilator V include disposable or rechargeable batteries 7 that are capable of operating under high capacity, wide temperature ranges and are compatible with the pneumatic subsystem N and the sensor subsystem S. In a preferred embodiment, the portable ventilator V of the present invention utilizes conventional lead-acid rechargeable batteries 7. The batteries 7 must provide at least 30 to 60 minutes of operating time.

Figure 5:
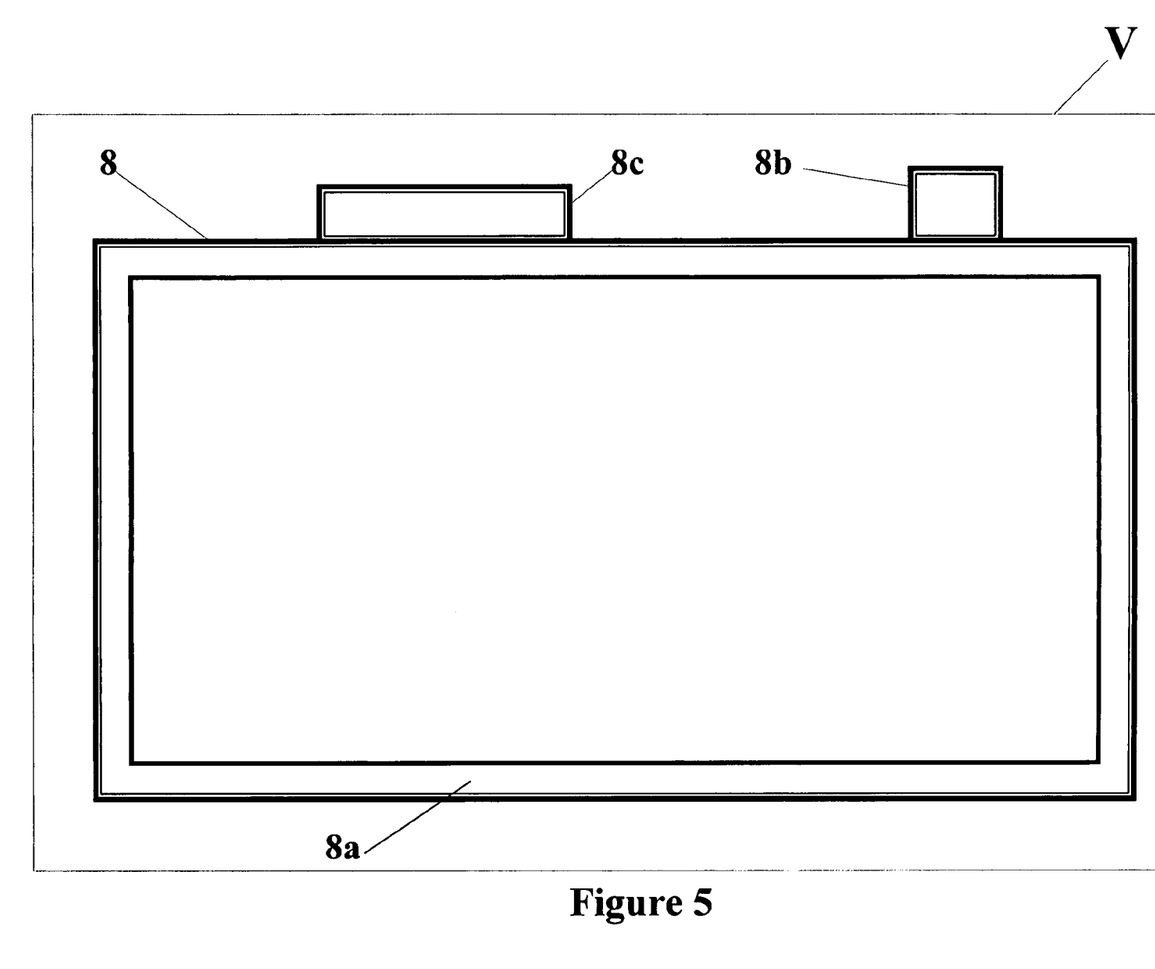
FIG. 5 is a drawing of the portable ventilator shown in FIG. 1.

The Portable Ventilator:

As shown in FIG. 5, the pneumatic subsystem N is connected to the sensor subsystem S and the power subsystem P and enclosed within housing 8 of the portable ventilator V. Housing 8 includes an rigid frame structure 8a that is made of either plastic or metals and capable of withstanding physical and mechanical pressures. Portable ventilator V includes an input port 8b that allows rechargeable batteries 7 to be powered using an external power source or an AC power source. Alternatively, batteries 7 may include disposable type batteries.

Housing 8 also a recessed control panel 8c. Control panel 8c includes ports for providing air to the user through known means. The panel 8c also includes a switch for selecting desired air flow rates, an on/off switch, and can include a switch for recharging the batteries 7. The control panel 8c is recessed to prevent damage to any instrumentation positioned thereon.

The portable ventilator V of the present invention implements controlled ventilation and assists control ventilation to a patient. Example 1 below shows functionality and performance of two portable ventilators V described above.

EXAMPLE 1

The Sekos 2 and 3 ventilators were tested. All tidal volumes, respiratory rates and other parameters were within ±10% of the settings existing on the ventilator V.

| PERFORMANCE PARAMETER | SEKOS 2 | SEKOS 3 |
|---|---|---|
| APPROX. WEIGHT (lb0 | 12 | <6 |
| APPROX. SIZE (in.) | 10.75 W × 9.75 D × 7 H | 5.7 W × 11.5 D × 3.5 H |
| PHYSICAL VOLUME (in$^3$) | 733 | 230 |
| BATTERY TYPE/SIZE | 3.4 Ah lead acid | 1.3 Ah lead acid |
| OPERATING LIFE (h) | 1.5-3 | 0.3-1 |
| COMPRESSORS | 2 | 2 |
| CONTROLLABLE I:E RATIO | No | No |
| RESP. RATE ADJUSTMENT (bpm) | 6-30 | 10 OR 20 ONLY |
| TIDAL VOLUME (ml) | 200-1200 | 300, 900, OR 1200 |
| MAX MINUTE VOLUME (L/m) | 20 (NOT YET TESTED) | 20 (NOT YET TESTED) |
| INSPIRATORY FLOW MEASUREMENT | No | No |
| EXPIRATORY FLOW MEASUREMENT | Yes | Yes |

The portable ventilators tested above, have been shown to be superior in performance to traditional "ambu-bags". These and other portable ventilators having the features discussed above are within the scope of this invention.

Figure 6:
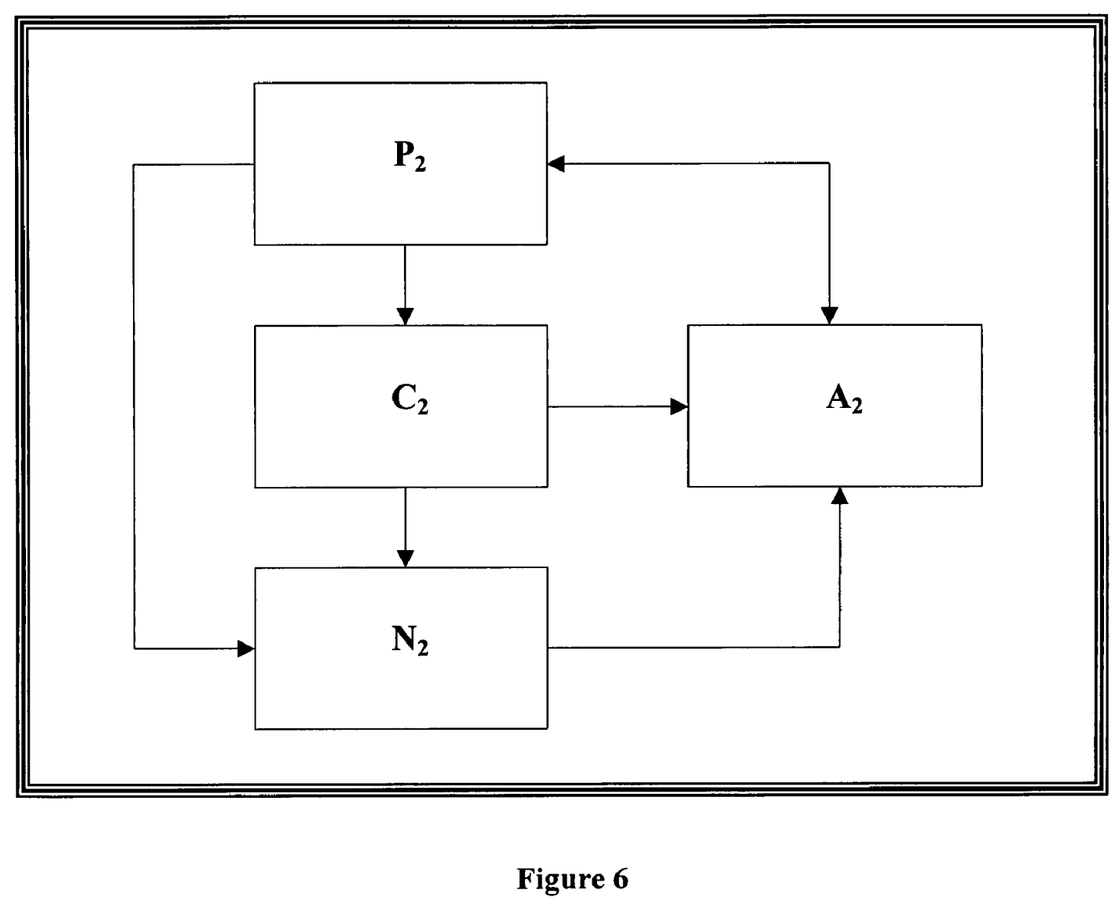
FIG. 6 is a schematic of the portable ventilator, the pneumatic subsystem, the power subsystem, the control subsystem and the alarm subsystem.

The present invention includes a preferred embodiment as shown in FIG. 6. The portable ventilator $V_2$, as shown in FIG. 6, includes a pneumatic subsystem $N_2$, a power subsystem $P_2$, a control subsystem $C_2$ and an alarm subsystem $A_2$.

Figure 6A:
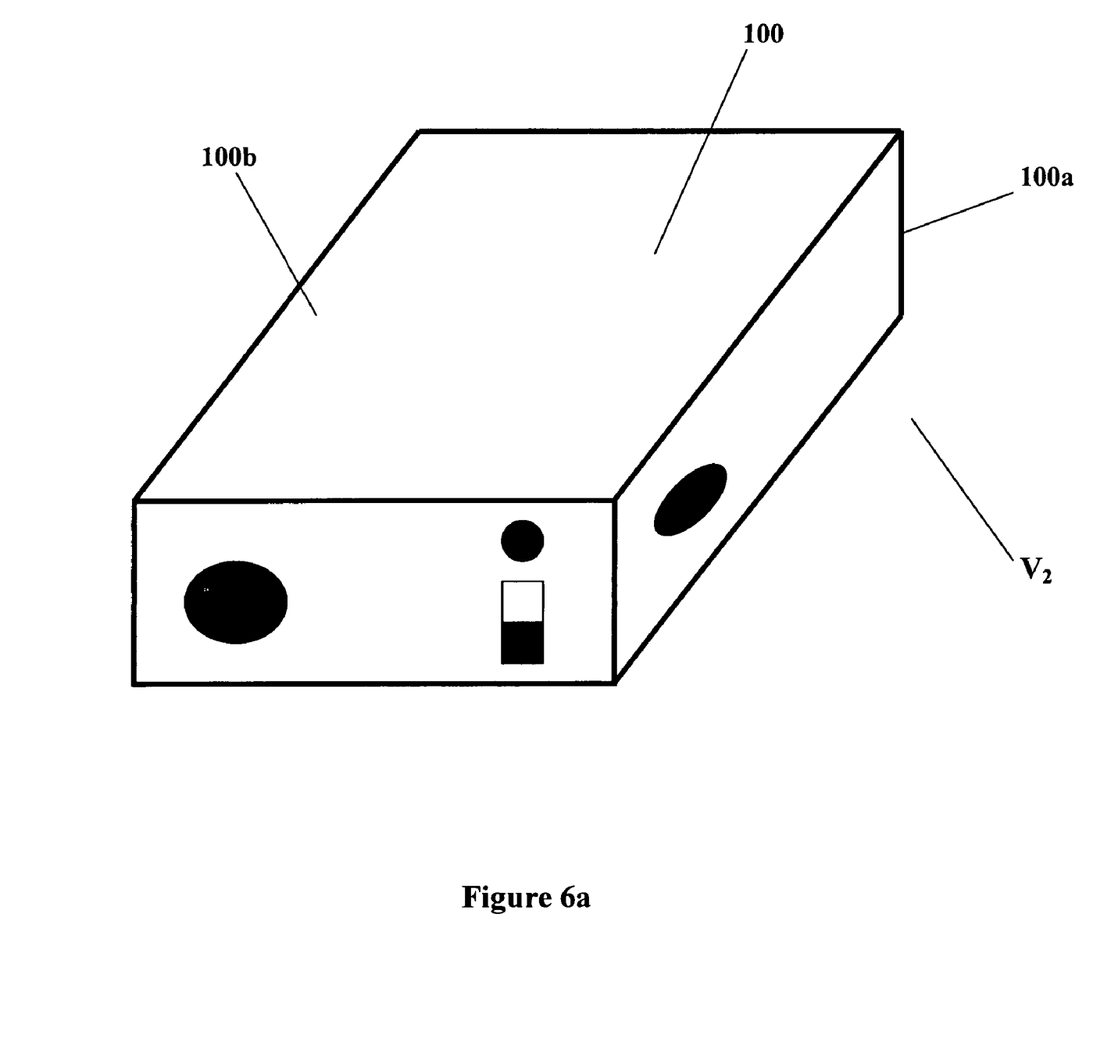
FIG. 6a is a drawing of the portable ventilator shown in FIG. 6.

The portable ventilator $V_2$ as shown in FIG. 6(a) includes a hard shell housing 100 having an exterior surface 100a and an interior surface 100b.

Figure 7:
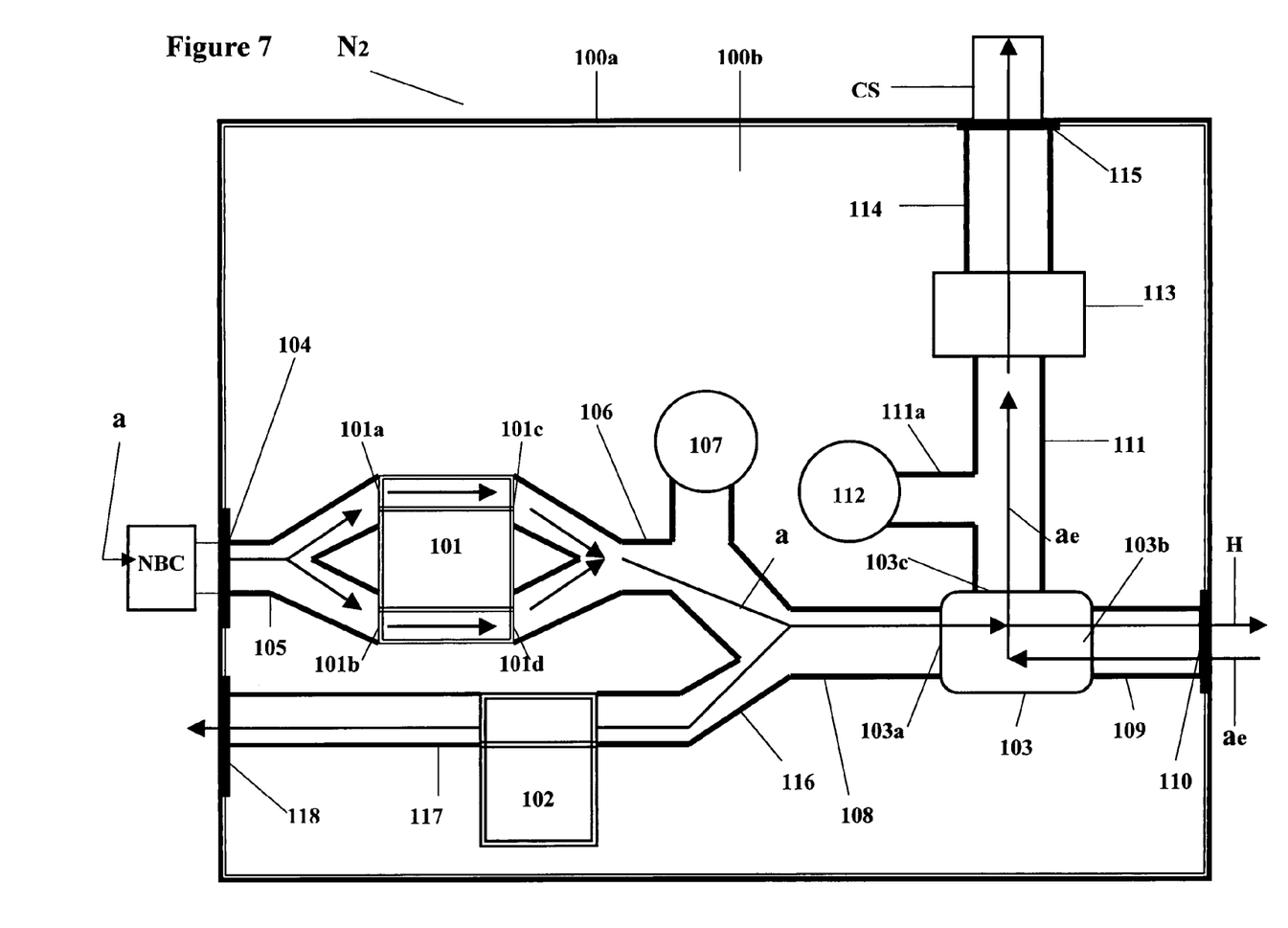
FIG. 7 is a schematic of the pneumatic subsystem shown in FIG. 6.

The Pneumatic Subsystem $N_2$:

As shown in FIG. 7, the pneumatic subsystem $N_2$ includes at least one dual head air compressor 101 for increased air output and a single head compressor 102 for closing a flutter valve 103. The pneumatic subsystem $N_2$ is responsible for the inhalation and exhalation cycles of the portable ventilator $V_2$. During the inhalation cycle, ambient air a is drawn into the dual head compressor 101 through the air input port 104. Ambient air a may also be passed through an NBC filter NBC to remove contaminants, before passing through air input port 104. Alternatively, a small adapter (not shown) may be connected to the air input port 104 to allow the ventilator $V_2$ to operate by drawing air a from a purified source (not pictured). Upon entering the portable ventilator $V_2$, ambient air a is divided into two air flow paths by y-shaped medical grade tubing 105. The tubing 105 may also be pre-manufactured plastic or metal. As is understood by one of ordinary skill in the art, tubing 105 includes all necessary fittings and attachments. Additionally, tubing 105 may be an integral part of an interior portion 100b of the hard shell housing 100, shown in FIG. 6a. Ambient air a enters the dual head compressor 101, from tubing 105, through dual-head compressor input ports 101a and 101b. Dual head compressor 101 compresses ambient air a. It is important to note that combination of using a dual head compressor 101 with a single head compressor 102 is critical to the portable ventilator $V_2$ of the preferred embodiment of this invention as disclosed in FIGS. 6 through 10. It is also important to note that multiple single head compressors in place of the dual head compressor 101, as disclosed in the preferred embodiment of FIGS. 6 through 10, are outside the scope of this present invention. This is because dual-head compressors provide for increased efficiency and smaller size. This factor is essential to the proper design and function of the portable ventilator $V_2$.

EXAMPLE 2

For an equivalent tidal volume output:

Dual Head Compressor: weight—14.2 oz, size—28.9 cubic inches.

2 Single Head Compressors: weight—20.4 oz, size—32.0 cubic inches.

Dual-head compressors draw in outside air and increase pressure within, to allow for the proper tidal volumes to be pushed through a small amount of space. Using the ideal gas law PV=nRT, where (P)=pressure, (V)=volume, (n)=number of molecules, (R)=gas law constant, and (T)=temperature, the values nRT must remain constant when dual head compressor 101 is operational. Thus, as necessitated by the proper operation of ventilator $V_2$, obtaining particular volumes (V) of air from the environment into a small, fixed volume of the ventilator $V_2$, requires that the pressure (P) of the air a must be increased to keep nRT the same. The increased pressure of air a forces the air a through the ventilator $V_2$ into the lungs of the patient H. This is due to the tendencies of fluids, here the compressed air a, to flow from the area of greater pressure of the ventilator $V_2$ to the area of lower pressure of the lungs of the patient H, thereby filling them.

As shown in FIG. 7, compressed air a exits the compressor 101 through compressor output ports 101c and 101d and into the air manifold 106. Air manifold 106 is manufactured from plastic or metal. Air manifold 106 may also be an integral part of the interior portion 100b. As is understood by one of ordinary skill in the art, air manifold 106 includes all necessary fittings and attachments. A pressure sensor 107 is connected to the air manifold 106 to monitor the pressure of air a delivered to the patient H. The pressure sensor 107 gauges the air pressure of compressed air a within air manifold 106. When air a exceeds a known threshold, the dual head compressor 101 is stopped and the single head compressor 102 is started, and air is no longer delivered to the patient H, as discussed below. As shown in FIG. 7, the air manifold 106 is also connected to the flutter valve 103. Flutter valve 103 allows compressed air a to enter through input port 103a and be delivered to the patient H through bi-directional port 103b. When compressed air a is being delivered to the patient H through bidirectional port 103b, exhale port 103c remains closed. When the patient H exhales however, the input port 103a is closed off, and exhale port 103c is open to allow exhaled air to be removed from the portable ventilator $V_2$. The exhalation cycle is described below. Compressed air a, that is delivered to the patient H, passes through medical grade tubing 108, flutter valve 103 and further through medical grade tubing 109 that is connected to the patient H through valve port 110. It is important to note that tubing 108 is integral to air manifold 106, and is shown in FIG. 7 as a separate element for descriptive purposes. Medical grade tubings 108 and 109 may also be pre-manufactured plastic or metal. As is understood by one of ordinary skill in the art, tubings 108 and 109 include all necessary fittings and attachments. Tubings 108 and 109 may be integral to interior portion 100b. A standard medical grade, patient endotracheal tube (not shown) or tubing to a respiratory mask (not shown) is connected between the portable ventilator $V_2$ and the patient H at patient valve port 110.

During the exhalation cycle, exhaled air a, is returned from the patient H through the patient valve port 110, tubing 109 and the bi-directional port 103b. The single head compressor 102 causes flutter valve 103 to close input port 103a, thereby directing the exhaled air $a_e$ into exhaust port 103c. Exhaled air $a_e$ passes from exhaust port 103c into medical grade tubing 111. Tubing 111 may be premanufactured plastic or metal and may be integral to interior portion 100b. As is understood by one of ordinary skill in the art, tubing 111 includes all necessary fittings and attachments. Tubing 111 includes a t-junction 111a that directs the exhaled air $a_e$ into a second pressure sensor 112. Second pressure sensor 112 verifies whether patient H is exhaling. In an alternate embodiment, t-junction 111a and pressure sensor 112 can be replaced with an in-line flow sensor (not shown). The exhaled air $a_e$ is directed to a patient exhale port 115, positioned on the ventilator housing 100. Prior to reaching the exhale port 115, the exhaled air $a_e$ is directed through an in-line capnography chamber 113. The capnography chamber 113 is used to detect the presence of exhaled $CO_2$ in exhaled air $a_e$. The exhaled air $a_e$ travels from the capnography chamber 113 through medical grade tubing 114. Tubing 114 may be premanufactured plastic or metal and may be integral to interior portion 100b. As is understood by one of ordinary skill in the art, tubing 114 includes all necessary fittings and attachments. An additional calorimetric or chemical capnography sensor CS may be connected externally to portable ventilator $V_2$ at exhale port 115, to further monitor ventilation efficiency. As shown in FIG. 7, the single head compressor 102, is connected to the flutter valve 103 and the air manifold 106 through medical grade tubing 116. It is important to note that tubing 116 is integral to air manifold 106, and is shown in FIG. 7 as a separate element for descriptive purposes. Tubing 116 may be premanufactured plastic or metal and may be integral to interior portion 100b. As is understood by one of ordinary skill in the art, tubing 116 includes all necessary fittings and attachments. The single head compressor 102 operates only when the dual-head compressor 101 is not running. The singlehead compressor 102 is used in this manner to ensure that the flutter valve input port 103a remains fully closed and the exhaust port 103c to be fully open in the exhalation cycle. This alternating operation of the dual head compressor 101 and the single head compressor 102 allows for dead volumes of air located in air manifold 106 to be evacuated through tubing 116, medical grade tubing 117 and exhaust port 118, between the inhalation cycles. Tubing 117 may be premanufactured plastic or metal and may be integral to interior portion 100b. As is understood by one of ordinary skill in the art, tubing 117 includes all necessary fittings and attachments. It is important to note that the single head compressor 102 functions to mechanically close flutter valve 103. This mechanism is preferred over electronically controlled valves, as they lead to pressure losses. This mechanism is preferred over other venting systems and pressure relief valves to reduce loss of inspiration air and pressure gradients. Secondly, use of the single head compressor 102 forcibly pulls air a out of air manifold 106, thereby allowing for the next inhalation cycle to begin unimpeded by dead air within air manifold 106. Thirdly, the single head compressor 102 provides a brief instance of negative pressure during the closure of input port 103a that assists the patient H to exhale.

In addition, the operation of this dual head compressor 101 and the single head compressor 102 precludes the use of the accumulator 2, as discussed in the embodiments of FIG. 1, above. In an alternate embodiment, single head compressor 102, tubing 117 and exhaust port 118 can be used to relieve pressure and/or heat buildup within the portable ventilator $V_2$. Exhaust port 118 also protects the portable ventilator $V_2$ from contamination in extreme environmental hazards, as well as contamination from water, dust, mud, etc.

It is important to note that the exhaust port 118 is positioned away from exhaust port 115 so as not to alter capnography measurements obtained from capnography sensors 113 and CS.

Figure 8:
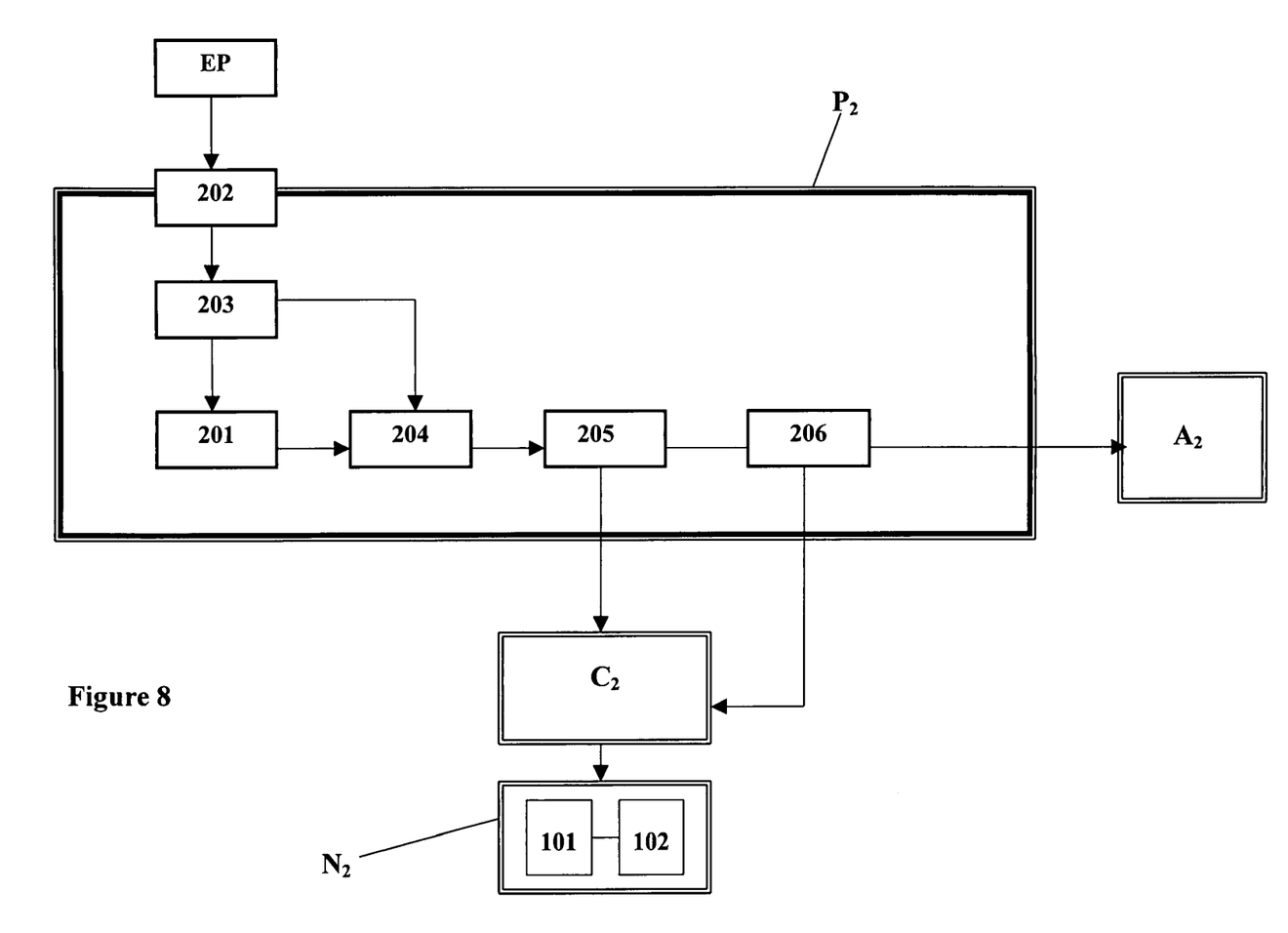
FIG. 8 is a schematic of the power subsystem shown in FIG. 6.

The Power Subsystem $P_2$:

The power subsystem $P_2$, as shown in FIG. 8, is discussed below. The power subsystem $P_2$ provides power to the portable ventilator $V_2$. The power subsystem $P_2$ includes a battery source 201 and a power jack 202 that accepts an external power source EP. A 12-14 volt rechargeable battery is preferred as the battery source 201. However, replaceable batteries may also be utilized. Power jack 202 is connected to electronic circuit 203 that is further connected to the battery source 201. The electronic circuit 203 accepts power from the external power source EP through the power jack 202 to regulate voltage necessary to recharge battery source 201 and/or bypass battery source 201. When an external power source EP is connected to the power jack 202, the by-pass from the electronic circuit 203 allows the portable ventilator $V_2$ to operate if battery 201 is missing, inoperational or recharging. Power is directed from either the battery 201 or the electronic circuit 203 into a power switch 204. When the power is turned on, it is directed from the power switch 204 to a voltage regulator circuit 205 that provides power for the subsystems within the ventilator $V_2$.

The power subsystem $P_2$ utilizes the voltage regulator circuit 205 to eliminate fluctuating voltages to the control subsystem $C_2$. For components in the control and alarm subsystems $C_2$ and $A_2$, respectively, that require a lower voltage, a second voltage regulator circuit 206 is utilized. Additionally, the power subsystem $P_2$ provides driving voltage through the control subsystem $C_2$ to the dual head compressor 101 and the single head compressor 102 of the pneumatic subsystem $N_2$.

Figure 9:
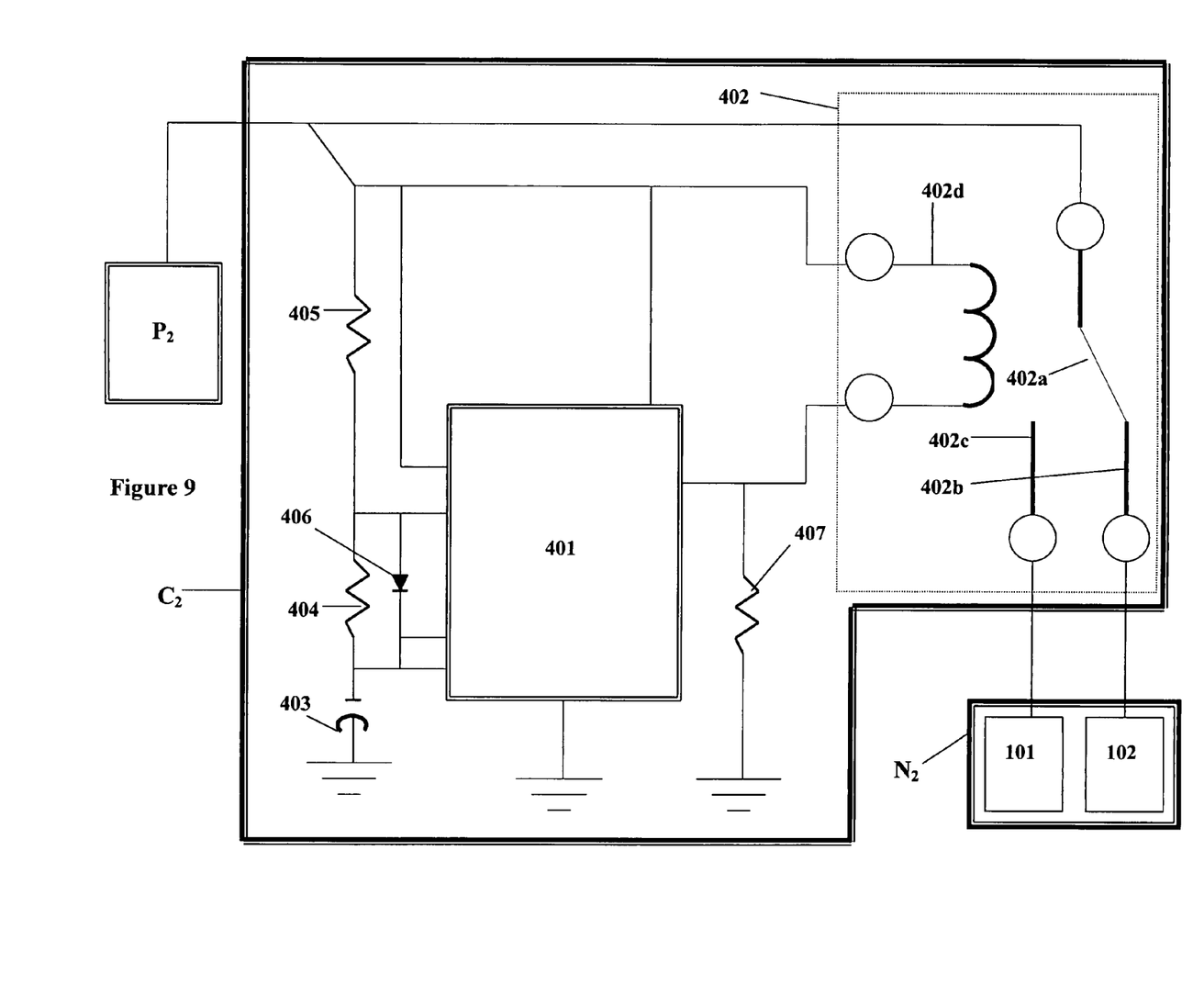
FIG. 9 is a schematic of the control subsystem shown in FIG. 6.

The Control Subsystem $C_2$:

As discussed under the pneumatic subsystem $N_2$ above, the on-off cycle between dual head compressor 101 and single head compressor 102 is critical to the operation of the preferred embodiment as shown in FIG. 6. As shown in FIG. 9, the control subsystem $C_2$ includes a timing circuit 401 that is used to control a mechanical relay switch 402 that in turn determines the on/off cycle between dual head compressor 101 and the single head compressor 102. The relay is configured as an electronically controlled single-pole double-throw switch 402. In a preferred embodiment, timing circuit 401 is a "555" circuit. The relay switch 402 is in turn connected to the single head compressor 102 of the pneumatic subsystem $N_2$ through a relay switch bar 402a and a first connector position 402b. Relay switch 402 and relay switch bar 402a are preferably mechanical. The relay switch 402 is also connected to the dual head compressor 101 through the switch bar 402a and second connector position 402c. The timing circuit 401 is connected to a relay control 402d, that is used to move the relay switch bar 402a between first connector position 402b and second connector position 402c, based upon a breath-timing cycle generated by the timing circuit. The breath-timing cycle is discussed below.

The timing circuit 401 is also connected to a capacitor 403, a first resistor 404 and a second resistor 405. Second resistor 405 is in turn connected to the power subsystem $P_2$. The connection between the power subsystem $P_2$ and the pneumatic subsystem $N_2$ is not shown in FIG. 9.

The breath-timing cycle is defined by the respiratory rate and the tidal volume, the values for which have been selected in accordance with American Medical Association guidelines.

Figure 9A:
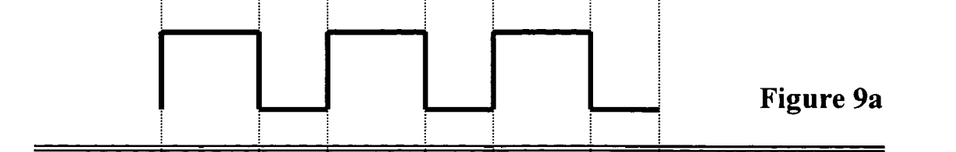
FIG. 9a is a graph of the dual head compressor on-off cycle.

As shown in FIG. 9a, $t_1$ represents the desired on time of compressor 101, correlating to the inhalation time, and $t_2$ represents the desired off time of compressor 101, correlating to the exhalation time. The sum of the inhalation and exhalation times ($t_1+t_2$) is one complete breath-timing cycle.

The respiratory rate is the number of complete breath-timing cycles per minute. The tidal volume is determined by the amount of air delivered during the inspiration phase in one breath-timing cycle. Tidal volume is the product of the flow rate of the compressor 101 by the on time $t_1$ of compressor 101. Therefore:

$$t_1 = TV/f \qquad (1)$$

where TV=tidal volume, f=flow rate of compressor 101;

$$t_1+t_2 = 60 \text{ seconds}/RR \qquad (2)$$

where RR=respiratory rate, the number of breaths per minute;

$$t_2 = 60/RR - t_1 = 60/RR - TV/f. \qquad (3)$$

The values for $t_1$ and $t_2$ are thus determined by using the AMA's respiratory rate and tidal volume guidelines, as well as the flow rate of compressor 101. Diode 406 is used to allow the possibility that $t_1$ less than $t_2$.

Figure 9B:
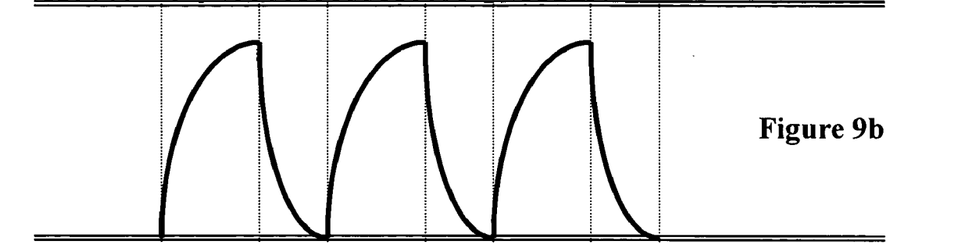
FIG. 9b is a graph of resistors and capacitor charging and discharging timing cycle.

As would be understood by one of ordinary skill in the art, the capacitor 403, first resistor 404 and second resistor 405 form a charging and discharging timing circuit. In the present invention, as shown in FIG. 9b, the charge cycle duration is selected to be equal to the desired inhalation time $t_1$. The discharge timing cycle is selected to be equal to the determined exhalation time $t_2$. Thus:

$$t_1 = 0.693(r_1+r_2)c_1 \text{ and} \qquad (4)$$

$$t_2 = 0.693(r_2)c_1; \qquad (5)$$

where $r_1$ is the value of the first resistor 404, $r_2$ is the value of the second resistor 405 and $c_1$ is the value of the capacitor 403.

Figure 9C:
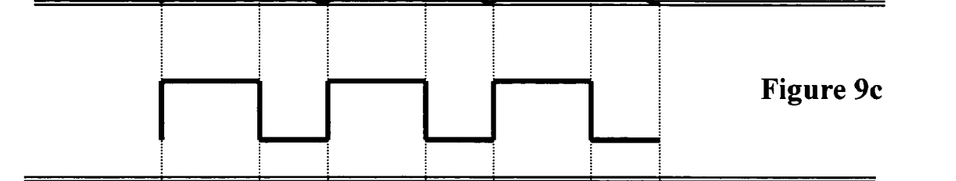
FIG. 9c is a graph of the output of the timing circuit.

Because the output of the charging and discharging circuit is indeterminate with respect to an on or off state of compressor 101, timing circuit 401 is utilized to establish a clear demarcation of on and off states, as shown in FIG. 9c, triggered by the output of the charging and discharging circuit.

It is important to note that timing circuit 401 is not powerful enough to operate compressors 101 and 102 directly. Therefore, the relay 402 is used where the output of timing circuit 401, as shown in FIG. 9c, is the control input to the relay 402. A resistor 407 is used to prevent an electrical short, when the output of timing circuit 401 is on.

Figure 9D:
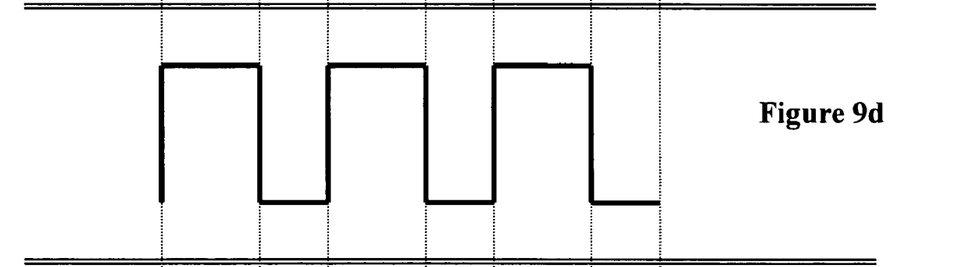
FIG. 9d is a graph of the higher power on-off cycle from the relay switch to the dual head compressor.

As shown in FIG. 9d, the output of the charging and discharging circuit from timing circuit 401 controls the relay 402 such that the on-cycle of circuit 401 causes the relay 402 to create a pathway to deliver a high power on-cycle to dual head compressor 101.

Figure 9E:
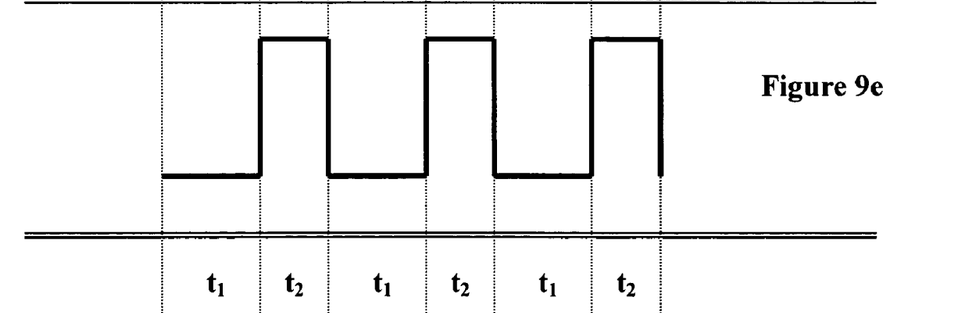
FIG. 9e is a graph of the higher power on-off cycle from the relay switch to the single head compressor.

As shown in FIG. 9e, the off-cycle of timing circuit 401 causes the relay 402 to create a pathway to single head compressor 102. The on-cycle of compressor 101 and off cycle of compressor 102 make up the on-off cycle discussed above.

It is also important to note that the timing characteristics, as shown in FIGS. 9c and 9d, must correspond to the desired timing characteristics in FIG. 9a for the proper operation of portable ventilator $V_2$.

Figure 10:
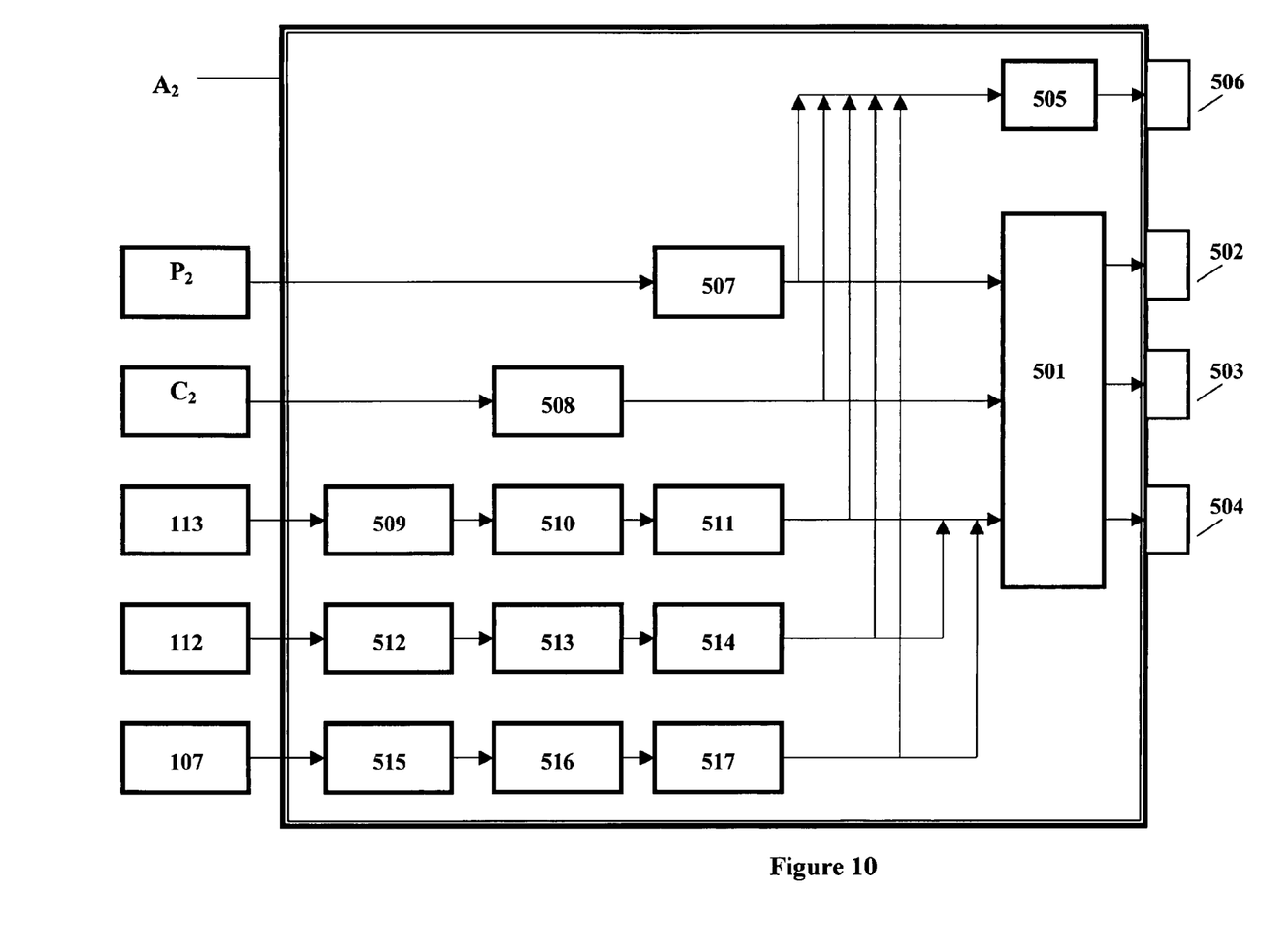
FIG. 10 is a schematic of the alarm subsystem shown in FIG. 6.

The Alarm Subsystem $A_2$:

As shown in FIG. 10, the alarm subsystem $A_2$ includes a light alarm suppression switch 501 connected to a repairable LED indicator 502, a non-repairable LED indicator 503 and a patient problem LED indicator 504. The LED indicators 502, 503 and 504 are configured to indicate repairable problems, non-repairable problems, and patient based problems, respectively, within the portable ventilator $V_2$. The LED indicators 502, 503 and 504 are positioned on the outer surface 100a of hard shell 100 of portable ventilator $V_2$. The alarm suppression switch 501 is accessible to the user U and used to disengage LED alarms 502, 503 and 504 when necessary. An audible alarm suppression switch 505 connected to an audible alarm switch 506. The audible alarm switch 506 is positioned on the outer surface 100a of hard shell 100. The audible alarm suppression switch 505 is accessible to the user U and used to disengage audible alarm 506 when necessary.

A low voltage detect circuit 507 is connected to the battery 201 and the power switch 205 of the power subsystem $P_2$ to indicate when voltage is too low. Low voltage detect circuit 507 is also connected to the light alarm suppression switch 501 and repairable LED indicator 502 to denote a repairable problem to the user U. The low voltage detect circuit 507 is also connected to the audible alarm suppression switch 505 and the audible alarm to indicate a sound-based alarm to the user U.

A missing pulse/device/component failure detect circuit 508 is connected to the control subsystem $C_2$. The missing pulse/device/component failure detect circuit 508 is also is also connected to the light alarm suppression switch 501 and non-repairable LED indicator 503 to denote a non-repairable problem to the user U, ie portable ventilator $V_2$ must be replaced. The missing pulse/device/component failure detect circuit 508 is also connected to the audible alarm suppression switch 505 and the audible alarm to indicate a sound-based alarm to the user U.

Carbon dioxide detect circuit 509 is connected to a carbon dioxide event counter 510 and a carbon dioxide event trigger 511. The circuit 509, counter 510 and trigger 511 is connected to the capnography sensor 113 of the pneumatic subsystem $N_2$ to indicate insignificant carbon dioxide concentrations in exhaled air $a_e$. The carbon dioxide event trigger 511 is further connected to the light alarm suppression switch 501 and patient problem LED indicator 502 to denote a improper connection or patient distress to the user U. The circuit 509, counter 510 and trigger 511 are also connected to the audible alarm suppression switch 505 and the audible alarm to indicate a sound-based alarm to the user U.

An exhale airflow detect circuit 512 is connected to an exhale event counter 513 and an exhale event trigger 514. The exhale circuit 512, event counter 513 and event trigger 514 is connected to the pressure sensor 112 of the pneumatic subsystem $N_2$. The exhale event trigger 514 is further connected to the light alarm suppression switch 501 and patient problem LED indicator 502 to denote a improper connection or patient distress to the user U. The exhale circuit 512, event counter 513 and event trigger 514 are also connected to the audible alarm suppression switch 505 and the audible alarm to indicate a sound-based alarm to the user U.

An inspiration pressure detect circuit 515 is connected to an inspiration event counter 516 and inspiration event trigger 517 to generate an alarm response when the ambient air, a, pressure is too high or too low. The inspiration circuit 515 is connected to the pressure sensor 107 of the pneumatic subsystem $N_2$. The inspiration event trigger 517 is further connected to the light alarm suppression switch 501 and patient problem LED indicator 502 to denote a improper connection or patient distress to the user U. The inspiration pressure detect circuit 515, inspiration event counter 516 and inspiration event trigger 517 are also connected to the audible alarm suppression switch 505 and the audible alarm to indicate a sound-based alarm to the user U. This inspiration pressure detect circuit 515 can also cause the relay control switch 402*d* to immediately switch from operating the dual head compressor 101 to operating the single head compressor 102 when a preset pressure threshold is exceeded, to prevent harm to patient H.

What is claimed is:

1. A portable ventilator system comprising:
   a hard shell device housing having an interior portion and an exterior surface;
   said interior portion including a power subsystem connected to a pneumatic subsystem, a control subsystem, and an alarm subsystem;
   said pneumatic subsystem comprising a dual head compressor connected to a single head compressor, said dual head compressor and said single head compressor constructed so as to operate at alternate times;
   said control subsystem comprising a timing circuit connected to a relay, said relay further connected to said single head compressor and said dual head compressor so as to control on and off cycle between said dual head compressor and allow said dual head compressor and single head compressor to operate at alternate times;
   said power subsystem comprising a battery source connected to an electronic circuit which in turn is connected to a power jack, so as to supply regulated power to said pneumatic, control and alarm subsystems, said electronic circuit and said power jack further constructed so as to connect to an external power source;
   said power subsystem further comprising a voltage regulator circuit so as to eliminate fluctuations in voltage to said control subsystem, said power subsystem also comprising a second voltage regulator circuit so as to supply lower voltages to said control and alarm subsystems;
   said alarm subsystem connected to said pneumatic subsystem and further comprising an LED patient problem indicator so as to detect patient problems within said pneumatic subsystem;
   said alarm subsystem further comprising a failure detect circuit connected to a non-repairable LED indicator, said circuit and non-repairable LED indicator connected to said control subsystem, so as to visually detect non-repairable problems within said control subsystem; and
   said alarm subsystem further comprising a low voltage detect circuit connected to a repairable LED indicator, said circuit and repairable LED indicator connected to said power subsystem and so as to visually detect repairable problems within said power subsystem.

2. A portable ventilator system as recited in claim 1 wherein said pneumatic subsystem further comprises a first input port constructed so as to allow ambient inhalation air to enter said ventilator;
   a first section of medical grade y-tubing constructed so as to divide said ambient inhalation air into two flow paths;
   said dual head compressor consisting of first and second input ports and first and second output ports, said input ports constructed so as to receive said ambient inhalation air from said y-tubing, said dual head compressor constructed so as to compress said ambient inhalation air, said first and second output ports further constructed as to dispel said compressed ambient inhalation air from said dual head compressor;
   an air manifold constructed so as to receive said compressed ambient inhalation air and dispel said compressed flutter valve, said first pressure sensor constructed so as to detect pressure of said ambient inhalation air;
   said flutter valve constructed so as to have a first inlet port so as to receive said compressed inhalation air, a second bi-directional port constructed so as to transfer said inhalation to a patient;
   said single head compressor constructed so as to allow said second port to also receive exhalation air from said patient;
   said flutter valve further constructed so as to transfer said exhalation air from said second port to a third outlet port, said outlet port constructed so as to allow said exhalation air to be monitored by a second sensor and transferred to a carbon dioxide detector, said single head compressor further constructed so as to remove dead air from said ventilator.

3. A portable ventilator system as recited in claim 2 wherein said control subsystem further comprises a first resistor connected to a second resistor and a capacitor so as to generate charging and discharging cycles;
   said timing circuit connected to said first resistor, said second resistor and said capacitor so as to establish on and off states corresponding to said charging and discharging cycles, said timing circuit further connected to said relay, said relay configured so as to provide increased power of said on-off states corresponding to on and off states of said timing circuit;
   said relay further comprising a relay control and a switch bar, said relay control constructed so as to switch said switch bar between a second connector position and a first connector position;
   said second connector position connected to said single head compressor so as to operate said single head compressor in said on and off cycle; and
   said first connector position connected to said dual head compressor, so as to operate said dual head compressor in said on and off cycle corresponding to said increased power on-off states.

4. A portable ventilator system as recited in claim 3 wherein said alarm subsystem further comprises a light alarm suppression switch and an audible alarm connected to an audible alarm suppression switch;
   said light alarm suppression switch constructed so as to suppress said non-repairable LED indicator, said repairable indicator and said patient problems indicator; and
   said audible alarm constructed so as to provide sound based alarms corresponding to repairable, non-repairable and patient problem indications, said audible alarm switch further constructed so as to bypass said audible alarm as necessary.

5. A portable ventilator system as recited in claim 4 wherein said second sensor comprises a pressure sensor.

6. A portable ventilator system as recited in claim 4 wherein said second sensor comprises a flow sensor.

7. A method of operating a portable ventilator comprising the steps of:
   (a) drawing ambient inhalation air into a dual head compressor,
   (b) compressing said ambient air in said dual head compressor and monitoring the pressure of said compressed air while maintaining a single head compressor in an off position;
   (c) transferring the compressed inhalation air into an air manifold and causing a flutter valve to open;
   (d) transferring said compressed inhalation air from said manifold to said flutter valve through an input port;
   (e) transferring said compressed inhalation air to a patient through a second bi-directional port in said flutter valve;
   (f) maintaining an exhale port of said flutter valve closed when operating said dual head compressor;
   (g) operating single head compressor to close off said input port and open exhale port, turning off said dual head compressor at the point when single head compressor is turned on, and allowing exhalation air from said patient to enter bi-directional port;
   (h) transferring exhalation air through said exhale port and verifying the presence exhalation air using a second sensor; and
   (i) removing exhalation air from said ventilator, through a patient exhale port.

8. A method of operating a portable ventilator as recited in claim 7 and further comprising the step of:
   measuring concentration of carbon dioxide in exhalation air using a capnography sensor.

9. A method of operating a portable ventilator as recited in claim 8 and further comprising the steps of
   (a) obtaining said on and off cycles using a timing circuit;
   (b) controlling on and off cycles for said dual head compressor and said single head compressor using a relay switch;
   (c) obtaining inhalation and exhalation cycles for the patient using said portable ventilator, said inhalation and exhalation cycles corresponding to said on and off cycles of said dual head and single head compressor;
   (d) providing visual and audible alarms corresponding to patient related problems; and
   (e) providing visual and audible alarms corresponding to ventilator repairable and non-repairable problems.

10. A method of operating a portable ventilator as recited in claim 9 comprising using a pressure sensor as said second sensor.

11. A method of operating a portable ventilator as recited in claim 9 comprising using a flow sensor as said second sensor.

* * * * *